United States Patent
Zink et al.

(10) Patent No.: US 8,124,070 B2
(45) Date of Patent: Feb. 28, 2012

(54) PROBIOTICS FOR PET FOOD APPLICATIONS

(75) Inventors: Ralf Zink, Le Mont Pelerin (CH); Roberto Reniero, Moyaux (FR); Florence Rochat, Montreux (CH); Christoph Cavadini, Le Mont Pelerin (CH); Thierry Der Weid, Lausanne (CH); Eduardo Schiffrin, Crissier (CH); Jalil Benyacoub, Lausanne (CH); Virginia Rousseau, Angers (FR); Pablo Perez, La Plata (AR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 12/823,659

(22) Filed: Jun. 25, 2010

(65) Prior Publication Data

US 2010/0266549 A1    Oct. 21, 2010

Related U.S. Application Data

(62) Division of application No. 11/701,916, filed on Feb. 2, 2007, now Pat. No. 7,771,982, which is a division of application No. 10/296,070, filed as application No. PCT/EP01/06039 on May 22, 2001, now Pat. No. 7,189,390.

(30) Foreign Application Priority Data

May 25, 2000  (EP) .................................... 00201867
Apr. 25, 2001  (EP) .................................... 01201503

(51) Int. Cl.
    *A01N 63/00*    (2006.01)
(52) U.S. Cl. .................................. 424/93.45; 435/252.9
(58) Field of Classification Search ........................ None
    See application file for complete search history.

(56) References Cited

U.S. PATENT DOCUMENTS

| 5,922,375 | A | 7/1999 | Luchansky et al. |
| 5,968,569 | A | 10/1999 | Cavadini et al. |
| 7,189,390 | B2 * | 3/2007 | Zink et al. .................. 424/93.45 |
| 7,771,982 | B2 * | 8/2010 | Zink et al. .................. 435/252.9 |

FOREIGN PATENT DOCUMENTS

| WO | WO 9608261 | 3/1996 |
| WO | WO 9917788 | 4/1999 |
| WO | WO 0053202 | 9/2000 |

OTHER PUBLICATIONS

International Search Report for International Application No. PCT/EP2001/06039 mailed Oct. 17, 2001.

* cited by examiner

*Primary Examiner* — Irene Marx
(74) *Attorney, Agent, or Firm* — K&L Gates LLP (57) ABSTRACT

The present invention relates to novel lactic acid bacterial micro-organisms that have been isolated and selected for their probiotic potential and their use for the preparation of petfood compositions intended to improve the health of pets, and to compositions containing the same.

2 Claims, 5 Drawing Sheets

PROBIOTICS FOR PET FOOD APPLICATIONS

CROSS-REFERENCE TO RELATED APPLICATIONS

This application is a divisional of patent application Ser. No. 11/701,916, filed Feb. 2, 2007, which is a divisional of patent application Ser. No. 10/296,070, filed Apr. 18, 2003, which is the U.S. national stage designation of International application no. PCT/EP01/06039 filed May 22, 2001, the entire content of which is expressly incorporated herein by reference.

FIELD OF THE INVENTION

The present invention relates to novel lactic acid bacteria and particularly micro-organisms of the genera *Lactobacillus*, *Bifidobacterium* and *Streptococcus* (*Enterococcus*) that have been isolated and selected for their probiotic potential. The present invention also relates to their use in the preparation of petfood compositions intended to improve the health of pets and to compositions containing the same. Methods of maintaining or improving pet health through feeding a pet such micro-organisms are also provided.

BACKGROUND

The well-being of domestic animals is closely related to their feeding. Correct feeding should result in a fit and healthy pet. In addition to providing nutritional value, food composition influences the intestinal microflora equilibrium and may lead to or prevent gastrointestinal disorders. Therefore, knowledge on the gastro-intestinal tract and digestion processes of healthy animals is integral to the understanding of a practical feeding practice. As meat-eaters, cats and dogs are characterized by a short digestive tract and a rapid flow rate of the bolus of food.

Among the constituents of the gastrointestinal microflora of cats and dogs *Bacteroides* sp., *Clostridium* sp., Enterobacteriaceae, *Bifidobacterium* sp., *Lactobacillus* sp., *Streptococcus* sp., *Staphylococcus* sp. and yeasts can be recovered.

The number and composition of this endogenous flora tend to be rather stable, although age and, to a lesser degree, food may modify it. Gastric acidity, bile, intestinal peristalsis and local immunity are factors thought to be important in the regulation of bacterial flora in the small intestine of human beings and various other mammals.

Often canine and feline gastrointestinal disorders are linked to bacterial overgrowth and the production of enterotoxins produced by pathogenic bacteria.

During the last few years research has focused on some valuable strains of lactic acid bacteria and their potential use as probiotic agents. Probiotics are considered to be viable microbial preparations which promote mammalian health by preserving the natural microflora in the intestine. Probiotics are thought to attach to the intestinal mucosa, colonize the intestinal tract and thereby prevent attachment of harmful micro-organisms thereon. A prerequisite for their action resides in that they have to reach the gut's mucosa in a proper and viable form and especially do not get destroyed by the influence of the low pH prevailing in the stomach. In particular, the physiology of the digestive tract of cats and dogs differs from humans. For example, the average pH in the stomach is about 3.4 for dogs and 4.2 for cats.

Although U.S. Pat. No. 5,968,569 discloses the inclusion of a probiotic micro-organism in a pet food cereal, neither it, nor the remaining available art provides information concerning strains specifically intended for pet health.

Consequently, there is a need to provide novel bacterial strains that are particularly adapted for pets and that have been selected for their high probiotic properties beneficial for pet health and to incorporate these strains into a pet food composition.

SUMMARY

According to a first aspect of the invention, there is provided a novel probiotic micro-organism of lactic acid bacteria, selected for its ability to survive and colonize the gastrointestinal tract of a pet and to exert a beneficial probiotic activity on pet health.

The probiotic strain may be selected from lactobacilli, bifidobacteria or Enterococci.

The probiotic strain may be selected from the group consisting of *Lactobacillus reuteri*, *Lactobacillus acidophilus*, *Lactobacillus animalis*, *Lactobacillus ruminis*, *Lactobacillus johnsonii*, *Lactobacillus casei*, *Lactobacillus paracasei*, *Lactobacillus rhamnosus*, *Lactobacillus fermentum* and *Bifidobacterium* spp., *Enterococcus faecium* and *Enterococcus* spp.

In a preferred embodiment the probiotic strain is selected from the group consisting of *Lactobacillus reuteri* (NCC2581; CNCM I-2448), *Lactobacillus reuteri* (NCC2592; CNCM I-2450), *Lactobacillus rhamnosus* (NCC2583; CNCM I-2449), *Lactobacillus reuteri* (NCC2603; CNCM I-2451), *Lactobacillus reuteri* (NCC2613; CNCM I-2452), *Lactobacillus acidophilus* (NCC2628; CNCM I-2453), *Bifidobacterium adolescentis* (e.g. NCC2627), *Bifidobacterium* sp. NCC2657 or *Enterococcus faecium* SF68 (NCIMB 10415).

The novel bacterial strain may be used in any amount from about 1.0E+04 to about 1.0E+12 cfu/animal and day and preferably from 1.0E+05 to about 1.0E+11 cfu/animal and day, most preferably from 1.0E+07 to 1.0E+10 cfu/animal and day.

In one aspect the invention relates to the use of the bacterial strain as described above and/or their supernatant of culture and/or their metabolites, for the preparation of a composition intended for the treatment and/or prophylaxis of disorders associated with the colonization of the gastrointestinal tract of pets by pathogenic micro-organisms. Unless the context clearly indicates otherwise, reference to "strain" should be understood to include its supernatant of culture and/or a metabolite thereof.

In another aspect, the invention relates to the use of the bacterial strain as described above and/or their supernatant of culture and/or a metabolite thereof, for the preparation of a composition intended for regulating the immune response of pets. By the term "regulating" the immune response, it is meant that the bacterial strains described above and/or their supernatant of culture and/or their metabolites have the capacity to either stimulate certain immune functions that are important to the pet's health or modulate other immune functions that could potentially be implicated in immune disorders, such as inflammation, allergy, etc. The stimulation or modulation of these immune functions can be achieved by using different combinations of the bacterial strains described above and/or their supernatant of culture and/or their metabolites.

The invention further provides a method of maintaining or improving the health of the gastrointestinal tract, the skin and/or coat system or the immune system of a pet comprising the step of feeding a pet a pet food composition containing at least one isolated strain as described above.

In addition, the invention provides a method for the treatment and/or prophylaxis of disorders associated with the colonization of the gastrointestinal tract of pets by pathogenic micro-organisms, comprising the step of feeding a pet a pet food composition containing at least one isolated strain according to the present invention.

The invention also provides a method of regulating the immune response in pets, comprising the step of feeding a pet a pet food composition containing at least one isolated strain according to the present invention.

The invention also provides a method of ameliorating or reducing the effects of ageing in a pet comprising the step of feeding a pet a pet food composition containing at least one isolated strain according to the present invention.

These selected micro-organisms have a particular beneficial impact on pets in their gastrointestinal tract, on their skin and/or coat, on their immune system, and on the effects of ageing.

They have a particular beneficial impact on intestinal pathogens such as strains *Salmonella typhimurium, Escherichia coli, Shigella dysenteriaea* or other pathogenic enterobacterieceae colonizing pets or parasites such as helminths (*Toxocara* spp.), protozoan (*Cryptosporidium* spp, *Giardia* spp., *Pentatrichomonas hominis, Entamoeba histolytica, Toxoplasma gondii*, . . . ) or yeasts.

Combined with food, these micro-organisms particularly exert their probiotic beneficial effects on palatability, digestion and gut health, immune function and sanitary conditions, the latter by way of contributing to a reduction of fecal volume and at least a partial deodorization of canine faeces. Thus, according to a second aspect of the invention, a petfood composition comprises a micro-organism having high probiotic activity in pets and being capable of surviving and colonizing the gastrointestinal tract of a pet ingesting it.

Accordingly, the invention relates to a petfood composition intended for the health of the gastrointestinal tract of pets, containing at least one probiotic strain isolated as described above and/or a supernatant of its culture and/or a metabolite thereof, associated with an ingestible support or a pharmaceutical matrix.

Also, the invention relates to a petfood composition intended for the regulation of the immune response of pets, containing at least one isolated strain as described above and/or a supernatant of its culture and/or a metabolite thereof, associated with an ingestible support or a pharmaceutical matrix.

Also, the invention relates to a petfood composition intended for ameliorating or reducing the effects of ageing in pets, containing at least one isolated strain as described above and/or a supernatant of its culture and/or a metabolite thereof, associated with an ingestible support or a pharmaceutical matrix.

Finally, the invention relates to a petfood composition intended for the health of the skin and/or coat of pets, containing at least one isolated strain as described above and/or a supernatant of its culture and/or a metabolite thereof, associated with an ingestible support or a pharmaceutical matrix.

In an embodiment, the ingestible support comprises a nutritionally balanced pet food composition. The said composition preferably contains sufficient amount of the isolated strain, it supernatant of culture and/or a metabolite thereof, to be effective in providing the said prophylactic effect when the composition is fed to a pet as a complete meal.

DETAILED DESCRIPTION

Within the following description, the abbreviation cfu ("colony-forming-unit") designates the number of bacterial cells as revealed by microbiological counts on agar plates.

Moreover, "NCC" designates Nestlé Culture Collection (Nestlé Research Center, Vers-chez-les-Blanc, Lausanne, Switzerland).

With respect to the first object of the present invention, 20 lactobacilli and 18 bifidobacteria isolated from cat and dog faeces, were screened and selected with regard to their technological and physiological parameters.

A first screening for potential probiotic applications was performed in-vitro (see examples 1 and 2): growth characteristics, tolerance to gastric acidity at different pHs and different concentrations of biliary salts present in the duodenum likely to be found in cats and dogs.

Furthermore, the good survival of freeze-dried cells in two different cryoprotective media was clearly demonstrated at 4° C. and 20° C. as indicated by an accelerated storage test.

These strains can be characterized by short generation times, high counts (more than 1.0E+08 cfu/ml) during their stationary phase and stability in high numbers at 8 and 24 h post-inoculation, stability to freeze-drying followed by either storage-conditions, resistance to physiological bile concentrations found in the duodenum (2% bile) and their low inhibition when grown in presence of up to 4% bile. Furthermore, results from DNA analyses were taken into account to select bacteria representative of the investigated diversity.

The strains intended for cat and dog health can grow up to at least 1.0E+06 cfu/ml in the presence of up to 2.0% bile salts. The strains can also grow up to at least 1.0E+06 cfu/ml after about 2 hours at a pH-range from about 3.4 to about 4.2.

The bacterial strains according to the invention may be selected from the group consisting of *Lactobacillus reuteri, Lactobacillus acidophilus, Lactobacillus animalis, Lactobacillus ruminis, Lactobacillus johnsonii, Lactobacillus casei, Lactobacillus paracasei, Lactobacillus rhamnosus, Lactobacillus fermentum, Bifidobacterium* sp., *Enterococcus faecium, Enterococcus* sp.

The following strains *Lactobacillus reuteri* NCC2581, *Lactobacillus rhamnosus* NCC2583, *Lactobacillus reuteri* NCC2592, *Lactobacillus reuteri* NCC2603, *Lactobacillus reuteri* NCC2613, and *Lactobacillus acidophilus* NCC2628 were deposited by the way of an example under the Budapest Treaty, at the Collection Nationale de Culture de Microorganismes, 25 rue du docteur Roux, 75724 Paris, France, on Apr. 19, 2000, under the following references CNCM I-2448, CNCM I-2449, CNCM I-2450, CNCM I-2451, CNCM I-2452 and CNCM I-2453, respectively. All restrictions as to the availability of these deposits will be withdrawn upon first publication of this application or another application which claims benefit of priority to this application.

Biochemical Characterization of the Selected Strains

*Lactobacillus reuteri* CNCM I-2448

Gram-positive micro-organism, non-motile, non-sporing

Fairly short and thick rodlets

Microaerophilic micro-organism with heterofermentative metabolism, production of L (+) and D (−) lactic acid.

Catalase (−), production of $CO_2$ from glucose, hydrolysis of arginine=$NH_3$ production Growth with 5% and 10% NaCl Fermentation of sugars: L-arabinose, galactose, D-glucose, lactose, saccharose, D-raffinose

*Lactobacillus* rhamnosus CNCM I-2449

Gram-positive micro-organism, non-motile, non-sporing

Fairly short and thick rodlets

Microaerophilic micro-organism with heterofermentative metabolism, production of L (+) lactic acid.

Catalase (−),

Fermentation of all sugars typical for *Lb. rhamnosus*

*Lactobacillus reuteri* CNCM I-2450

Gram-positive micro-organism, non-motile, non-sporing
Fairly short and thick rodlets
Microaerophilic micro-organism with heterofermentative metabolism, production of L (+) and D (−) lactic acid.
Catalase (−), production of $CO_2$ from glucose, hydrolysis of arginine=$NH_3$ production
Growth with 5% and 10% NaCl
Fermentation of sugars: L-arabinose, galactose, D-glucose, D-xylose, lactose, saccharose, D-raffinose
*Lactobacillus* reuteri CNCM I-2451
Gram-positive micro-organism, non-motile, non-sporing
Fairly short and thick rodlets
Microaerophilic micro-organism with heterofermentative metabolism, production of L (+) and D (−) lactic acid.
Catalase (−), production of $CO_2$ from glucose, hydrolysis of arginine=$NH_3$ production
Growth with 5% and 10% NaCl
Fermentation of all sugars which are typical for *Lb. reuteri*
*Lactobacillus reuteri* CNCM I-2452
Gram-positive micro-organism, non-motile, non-sporing
Fairly short and thick rodlets
Microaerophilic micro-organism with heterofermentative metabolism, production of L (+) and D (−) lactic acid.
Catalase (−), production of $CO_2$ from glucose, hydrolysis of arginine=$NH_3$ production
Growth with 5% and 10% NaCl
Fermentation of sugars: L-arabinose, D-glucose, lactose, saccharose, D-raffinose
*Lactobacillus reuteri* CNCM I-2453
Gram-positive micro-organism, non-motile, non-sporing
Fairly short and thick rodlets
Microaerophilic micro-organism with homofermentative metabolism, production of L (+) and D (−) lactic acid.
Catalase (−),
Fermentation of sugars: D-glucose, lactose, saccharose, D-raffinose Three lactobacilli isolated from cats (NCC2581, NCC2592, NCC2583), three lactobacilli from dogs (NCC2603, NCC2613, NCC2628), one bifidobacteria from cats (NCC2627) and one bifidobacteria from dogs (NCC2657) were further tested for their probiotic potential activity in pets (see examples 3 and 4).

In another embodiment, the present invention relates to the use of bacterial strains as described above, for the preparation of a food composition capable of improving or maintaining pet health.

They can be used in their viable form, inactivated form, as a supernatant of a culture or fractions thereof, e.g. cell walls, peptidoglycan, cytoplasm, purified proteins, functional metabolites, bioactive molecules.

They are preferably used in an amount of from about 1.0E+04 cfu/g to about 1.0E+11 cfu/g and preferably from 1.0E+05 cfu/g to about 1.0E+10 cfu/g, most preferably from 1.0E+06 cfu/g to 1.0E+09 cfu/g.

In a preferred embodiment, they may be used as dietary adjuncts so as to improve pet food quality and may be included in an amount of from about 1.0E+04 cfu/g to about 1.0E+11 cfu/g. As dietary adjuncts, they may be encapsulated or may be provided in powder form and packaged in conjunction with or separately from a main meal, be it wet or dry. By way of example, a powder containing selected micro-organisms according to the invention, or components or moieties of the supernatant of their cultures or selected metabolites, may be packed in sachets in a powder form or in a gel or lipid or other suitable carrier. These separately packaged units may be provided together with a main meal or in multi-unit packs for use with a main meal or treat, according to user instructions.

In another example, the probiotic strain/s may be provided in a multi-chamber packaging unit together with a second ingestible component, for example a wet or medium moisture content chunky meal or a meal-sized batch of dried kibbles in a flexible pouch configuration. A first chamber in the pouch would contain the probiotic strain and a second, separate sealed chamber the second ingestible component.

These selected micro-organisms have a particular beneficial impact in pets on their gastrointestinal tract, on their skin and/or coat, on their immune system, on dental or oral health, on their bones and on the effects of ageing.

They are also found to improve palatability of food, digestion, immune function and sanitary conditions (reduction of fecal volume and partial deodorization of canine faeces) in pets.

The present invention also relates to a pet food composition for improving or maintaining the health of pets containing at least one probiotic strain having the above traits, associated with an ingestible support or a pharmaceutical matrix.

At least one bacterial strain having the above traits and/or its supernatant of culture or a fraction thereof and/or its metabolites may be administered to the pet as a supplement to the its normal diet or as a component of a nutritionally complete pet food.

The nutritionally complete pet food composition according to the invention may be in powdered, dried form or a wet, chilled or shelf stable pet food product. These pet foods may be produced by ways known in the art provided that where micro-organism activity is desired, care is taken to ensure survival of the micro-organism. Apart from the bacteria strains and/or its fermented medium, these pet foods may include any one or more of a starch source, a protein source and lipid source.

Suitable starch sources are, for example, grains and legumes such as corn, rice, wheat, barley, oats, soy, and mixtures of these.

Suitable protein sources may be selected from any suitable animal or vegetable protein source; for example meat and meal, poultry meal, fish meal, soy protein concentrates, milk proteins, gluten, and the like. For elderly animals, it is preferred for the protein source to contain a high quality protein.

Suitable lipid sources include meats, animal fats and vegetable fats.

The choice of the starch, protein and lipid sources will be largely determined by the nutritional needs of the animal, palatability considerations, and the type of product applied. For elderly pets, the pet food preferably contains proportionally less fat than pet foods for younger pets. Furthermore, the starch sources may include one or more of rice, barley, wheat and corn.

Further, various other ingredients, for example, sugar, salt, spices, seasonings, vitamins, minerals, flavouring agents, fats and the like may also be incorporated into the pet food as desired.

For dried pet foods a suitable process is extrusion cooking, although baking and other suitable processes may be used. When extrusion cooked, the dried pet food is usually provided in the form of a kibble. If a prebiotic carbohydrate is used, the prebiotic may be mixed with the other ingredients of the dried pet food prior to processing. A suitable process is described in European patent application No 0850569; the disclosure of which is incorporated by reference. If a probiotic micro-organism is used and activity is desired in the final product, the organism is best coated onto or filled into the dried pet food. A suitable process is described in European patent application No 0862863; the disclosure of which is incorporated by reference. Where survival of the micro-organism is not required, it may be added to the pre-extrusion mix, as may the supernatant of its culture or metabolite, as desired.

For wet foods, the processes described in U.S. Pat. Nos. 4,781,939 and 5,132,137 may be used to produce simulated meat products. The disclosures of these patents are incorporated by reference. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers. As in the case of producing dried pet foods, where survival of the probiotic species chosen is not essential, it may be added to the feed mix prior to cooking or heating, or at any appropriate or convenient stage in the production process.

The amount of prebiotic in the pet food is preferably less than about 20% by weight and further preferably less than about 10% by weight. For example, the prebiotic may comprise from about 0.1% to about 5% by weight of the pet food. For pet foods which use chicory as the prebiotic, the chicory may be included to comprise from about 0.5% to about 10% by weight of the feed mixture; more preferably from about 1% to about 5% by weight.

The pet foods may contain other active agents such as long chain fatty acids. Suitable long chain fatty acids include alpha-linoleic acid, gamma-linoleic acid, linoleic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma-linoleic acid. Safflower oils, sunflower oils, corn oils and soy bean oils are suitable sources of linoleic acid.

If necessary, the pet foods are supplemented with minerals and vitamins so that they are nutritionally complete.

Furthermore, if desired, the bacteria strain may be encapsulated; for example in a sugar matrix, fat matrix or polysaccharide matrix. It may also be coated as described in EP 862 863.

The novel probiotic strain is preferably used so that the pet food preferably contains about 1.0E+04 to about 1.0E+10 cells of the probiotic micro-organism per gram of the pet food; more preferably about 1.0E+06 to about 1.0E+08 cells of probiotic micro-organism per gram. The pet food may contain about 0.005% to about 10% by weight of the mixture of the probiotic micro-organism. It preferably contains about 0.02% to about 6% by weight and most preferably about 1% to about 6% by weight.

The amount of pet food to be consumed by the pet to obtain a beneficial effect will depend on the size or the pet, the type of pet, and age of the pet. However, an amount of the pet food to provide a daily amount of about 1.0E+03-1.0E+14 cfu of at least one lactic acid bacteria strain and/or the equivalent fermentation medium, would usually be adequate. Preferably about 1.0E+09 to 1.0E+11 cfu/day for dogs or 1.0E+07 to 1.0E+10 cfu/day for cats are administered.

The composition according to the invention has a high probiotic activity and/or is found to be particularly effective for improving and/or maintaining healthy digestive function in pets, and improving and maintaining the gastrointestinal tract, skin and/or coat, and/or immune system, health of pets. This composition has also a beneficial impact on effects of ageing in cats and dogs.

The present invention is not to be limited in scope by the specific embodiments described herein. The examples are preceded by a brief description of the figures.

EXAMPLES

Example 1

Strains and Culture Conditions

Numerous strains (from the Nestlé culture collection=NCC) were screened for their potential probiotic use for cats and dogs. In particular, growth potentials, resistance to freeze-drying with subsequent storage, tolerance to gastric acidity and different concentrations of bile salts found in the gastrointestinal tract of cats and dogs, were assessed for those 20 lactobacilli and 18 bifidobacteria isolated from cat and dog faeces presented in Table 1.

TABLE 1

Codes and characteristics of bacteria selected for the assays

*Lactobacilli*:

| NCC-Code | CNCM-Code | Code | Animal species origin | Type of diet intake | NH3 from arginine | Lactic acid | Identified with API50CH |
|---|---|---|---|---|---|---|---|
| 2578 | — | LB1-1 | Cat | Mixed | − | L | *L. animalis/ruminis* |
| 2581 | I-2448 | LB1-2 | Cat | Mixed | + | D/L | *L. reuteri* |
| 2583 | I-2449 | LK1-1 | Cat | Mixed | − | D/L | *L. rhamnosus* |
| 2586 | — | LK1-2 | Cat | Mixed | + | D/L | *L. reuteri* |
| 2590 | — | LH2-1 | Cat | Dry | − | D/L | *L. acidophilus* |
| 2592 | I-2450 | LR1-1 | Cat | Mixed | + | D/L | *L. reuteri* |
| 2594 | — | LS1-1 | Cat | Mixed | − | L | *L. animalis/ruminis* |

TABLE 1-continued

Codes and characteristics of bacteria selected for the assays

| | | | | | | | |
|---|---|---|---|---|---|---|---|
| 2597 | — | LA2-5 | Dog | Wet | − | L | L. animalis |
| 2600 | — | LC2-5 | Dog | Wet | − | D/L | L. fermentum/reuteri |
| 2603 | I-2451 | LE2-5 | Dog | Wet | − | L | L. reuteri |
| 2606 | — | LF2-6 | Dog | Dry | + | D/L | L. reuteri |
| 2609 | — | LH2-6 | Dog | Dry | + | D/L | L. reuteri |
| 2613 | I-2452 | LH2-7 | Dog | Dry | + | D/L | L. reuteri |
| 2616 | — | L1-1-1 | Dog | Mixed | + | D/L | L. reuteri/fermentum |
| 2619 | — | L1-1-2 | Dog | Mixed | − | D/L | L. acidophilus |
| 2621 | — | L3-1-2 | Dog | Mixed | − | L | L. animalis/ruminis |
| 2625 | — | L7-1-3 | Dog | Mixed | − | L | L. animalis/ruminis |
| 2628 | I-2453 | LA1-5 | Dog | Mixed | − | D/L | L. acidophilus |
| 2632 | — | LA1-6 | Dog | Mixed | + | D/L | L. reuteri/fermentum |
| 2636 | — | LB1-5 | Dog | Mixed | − | L | L. animali/ruminis |

Bifidobacteria:

| NCC Code | Code | Animal species origin | Type of diet intake | Species |
|---|---|---|---|---|
| 2623 | CO2-5 | Cat | Dry | Bifidobacterium |
| 2627 | CG2-5 | Cat | Dry | Bif. adolescentis |
| 2630 | CH2-5 | Cat | Dry | Bif. adolescentis |
| 2533 | CE3-1 | Cat | Dry | Bif. adolescentis |
| 2635 | CC1-5 | Cat | Mixed | Bif. longum/suis |
| 2637 | CE4-1 | Cat | Dry | Bif. adolescentis |
| 2640 | CB3-5 | Cat | Dry | Bif. adolescentis |
| 2643 | CJ2-6 | Cat | Dry | Bif. adolescentis |
| 2647 | D5-3-5 | Dog | Wet | Bif. adolescentis |
| 2651 | D8-3-6 | Dog | Dry | Bif. animalis/lactis |
| 2654 | D9-3-7 | Dog | Dry | Bif. animalis/lactis |
| 2657 | D6-3-6 | Dog | Dry | Bifidobacterium |
| 2660 | D7-3-5 | Dog | Dry | Bifidobacterium |
| 2663 | DB3-1 | Dog | Dry | Bifidobacterium |
| 2667 | DC3-1 | Dog | Dry | Bifidobacterium |
| 2671 | DA1-3 | Dog | Mixed | Bif. animalis/lactis |
| 2574 | DA3-1 | Dog | Dry | Bifidobacterium |
| 2677 | DD3-1 | Dog | Dry | Bif. adolescentis |

All 20 lactobacilli and 18 bifidobacteria were isolated from cats and dogs kept on different diets, as shown in Table 1. Initial identification was determined by morphological and physiological characteristics. API-50CH and Rapid-ID32A systems (BioMérieux) were used for lactobacilli and bifidobacteria, respectively. Pure strains were frozen and deposited at −80° C. in the Nestec-Culture-Collection (NCC).

All bacteria were cultured in broth-medium for the assays. A sample from each reactivated strain was stored at −80° C. in 1 ml-cryoprotective media (40% glycerol+60% LL). The cultures were maintained by subculturing on a weekly base a 1% inocula in 10 ml-growth medium and anaerobic incubation at 37° C.

*Lactobacilli* were grown in MRS for 18 hours. Bifidobacteria were grown either in MRS+0.05% (w/v) L-cysteine hydrochloride (MRS-C) for 32 hours or in BHI+0.05% L-cysteine hydrochloride (BHI-C) for 48 hours starting with a 5% inoculum.

All cultures were stored at +4° C. between the different transfers. Anaerobiosis was generally obtained using a hydrogen-carbon dioxide anaerobic system (GasPak, Becton Dickinson, USA). Bifidobacteria were always kept in these jars during their storage period.

Example 2

Selection of Bacterial Strains

This in-vitro screening was based on production characteristics for an industrial application of viable cells, their ability to survive inhibiting or detrimental gastro-intestinal conditions and their genomic diversity. Strain diversity or genomic similarity of those non-characterized strains was taken into account, using RAPD and ribotyping.

Materials and Methods

Bacterial Growth

The strains that are able to produce rapidly high number of cells have to be identified. Their bacterial growth cycle can be characterized by a short lag phase, a short generation time, high maximal counts and a long stationary phase. Therefore, strains were compared by considering three variables: the length of their lag phase, their generation time (in hours) and their maximal counts, which corresponded to the most important characteristics.

For *Lactobacilli*:

200 ml MRS broth preincubated at 37° C. was inoculated with 1% of a fresh subculture. One ml samples were collected at every hour post-inoculation for eight hours. A final sample was taken after 24 h. One ml of each sample was 10-fold serially diluted in TS for enumeration. Cultures were grown in MRS agar (pour-plating technique), anaerobically, at 37° C., for 48 hours. All plates with colony-numbers between 30 and 350 were recorded as colony forming units (cfu) per ml of culture and were therefore taken into consideration for enumerations.

For Bifidobacteria in (MRS-C):

In preliminary assays, all strains were enumerated after 24 h growth in MRS-C and TPYG broth. Results were expressed in cfu/ml. The growth curves were established by determining the cell numbers when grown in MRS-C after 0, 4, 12, 24, 32 and 48 h, according to the protocol described for lactobacilli. In order to determine the influence of the subculture medium and of optimization of degassing the growth medium, this assay was realized:

from a subculture, in BHI-C stored 48 h at 4° C., and inoculated in MRS-C from a subculture, in BHI-C stored 48 h at 4° C., and inoculated in MRS-C well degassed (removal of oxygen had been optimized by autoclaving the medium twice and storing it directly in anaerobic jars)

from a fresh subculture, in MRS, and inoculated in MRS-C well degassed and stored under anaerobic conditions before the experiment

TABLE 2

Test media for bacterial growth

| Substrate | Composition | | pH | References |
|---|---|---|---|---|
| *For lactobacilli* | | | | |
| MRS | MRS without sugar (Difco) | 35 g·l$^{-1}$ | 6.5 | De Man and al. (1960) |
| | Glucose | 20 g·l$^{-1}$ | | |
| | Distilled water | 1,000 ml | | |
| *For bifidobacteria* | | | | |
| MRS-C | MRS without sugar (Difco) | 35 g·l$^{-1}$ | 6.0 | Pacher and Kneifel (1996) |
| | Glucose | 20 g·l$^{-1}$ | | |
| | L-cysteine HCl (Fluka) | 0.5 g·l$^{-1}$ | | |
| | Distilled water | 1,000 ml | | |
| TPYG (Trypticase Peptone Yeast Extract) | Trypticase (BBL) | 50 g·l$^{-1}$ | 7.0 | |
| | Peptone (Difco) | 5 g·l$^{-1}$ | | |
| | Yeast extract (Difco) | 20 g·l$^{-1}$ | | |
| | Glucose (Merck) | 4 g·l$^{-1}$ | | |
| | L-cysteine HCl (Fluka) | 1 g·l$^{-1}$ | | |
| | Distilled water | 1,000 ml | | |

Solid media were obtained by the addition of Difco Bacto agar (15 g·l$^{-1}$). Media were autoclaved at 121° C. for 15 min. Liquid media for bifidobacteria were either stored under anaerobic conditions or degassed before utilization.

Resistance to Gastric pH and Bile

When ingested, the micro-organisms have to survive stomach and duodenum conditions to be able to exert a beneficial activity in the gastro-intestinal tract of the animal. Gastric pH and biliary salts are the main components responsible for regulation of bacterial flora. Therefore, the degree of resistance of the strains to acidity and bile has to be assayed.

The physiology of the digestive tract of cats and dogs differ from humans. The average pH were pH 3.4 and 4.2 respectively in dogs and cats. A reconstituted pet bile was recommended for the assays (Table 4). The bile concentration in the small intestine varies in a range of 0.5 to 2% when food is digested.

According to extreme pH values found in cats and dogs, viable counts after 10 minutes at pH 2.6 and after two hours at either pH 3.4 (strains isolated from dogs) or pH 4.2 (strains isolated from cats) should not be below 1.0E+06 cfu/ml.

Resistance to Gastric pH

All lactobacilli were inoculated at 1% in MRS broth and grown anaerobically at 37° C. overnight. Bifidobacteria, inoculated at 5% in BHI-C, were grown 48 hours at 37° C. under anaerobic conditions. The cultures were dispensed in two ml reaction tubes (Eppendorf) and centrifuged at 3,500× g/10 min/20° C. Cells were washed three times with Ringer-solution. The resistance to stomach acidic conditions was assayed in-vitro in three simulated gastric juices with pH levels of 2.6, 3.4 and 4.2 adjusted with HCl (Merck). Disposable filterware (Nalgene) was used for all filter-sterilizations. The survival of each bacterial suspension was studied by adding one ml into a series of five ml of simulated gastric juice (different pHs) supplemented with 1.5 ml of a 0.5% NaCl solution.

The samples were incubated at 37° C. and the viable organisms enumerated at:

0, 1, 5, 10 minutes with the pH 2.6 gastric juice 0, 1, 30, 60, 120, 180 minutes when the gastric juice had a pH of either 3.4 (for strains isolated from dogs) or 4.2 (for strains isolated from cats)

Samples were diluted in phosphate buffer (pH 7.0), plated onto MRS-C agar and enumerated.

TABLE 3

Simulated gastric juice

| Substrate name | Composition | PH |
|---|---|---|
| Gastric juice | 0.3% w/v porcine pepsin (Sigma) 0.5% w/v NaCl HCl (Merck): to adjust pH | 2.1, 3.4 or 4.2 |

Resistance to Bile Salts

The evolution of the viable counts of lactobacilli grown for 18 hours in presence of various concentrations of reconstituted pet bile was determined.

Two viable counts were considered significantly different when the deviation of their $\log_{10}$ was above 0.25. Each strain was characterized by two variables:

the maximal bile salt concentration tested where no significative difference with the control was found the rate of the decrease in viability when bile concentration in the growth medium increases The strains characterized by a loss superior to a $\log_{10}$ of their viable counts when bile concentration raises in 1% steps were considered sensitive to bile. A reduction superior to one $\log_{10}$ between cells grown in presence of 0 and 2% bile, and to one $\log_{10}$ per additional percent of bile (above 2%) was considered acceptable. Furthermore, only strains producing more than 1.0E+06 cfu/ml when grown in presence of up to 2% bile salts should be selected, in order to produce an effect in the gastrointestinal tract.

Reconstituted pet bile from cats or dogs was prepared as indicated in Table 4, and filter sterilized prior to use. In a first assay, lactobacilli were grown anaerobically for 24 hours in MRS broth at 37° C. and transferred into fresh MRS broth plus 0, 0.1, 0.3, 0.5, 1, 2, 4% sterile reconstituted pet bile for additional 18 hours. Samples were 10-fold serially diluted in TS for enumeration. Dilutions 1.0E-03 and 1.0E-05 were plated onto MRS agar, using a WASP (<<Whitley Automatic Spiral Plater>>; Don Whitley Scientific Limited, England). When dried, the plates were inverted and incubated 48 hours at 37° C. in anaerobic jars.

Floch and al. (1972) defined an inhibition as significant when at least 2 logs in the test compared with the control tube growth were reduced. Based on this, all the lactobacilli sensitive to bile concentrations in the first assay and two lactobacilli resistant to 4% bile were tested similarly in presence of 0, 1, 1.5, 2, 2.5, 3, 4% bile. The second test aimed for a repeatability and established if the number of viable bacteria decreased dramatically with increasing bile concentration.

On the other hand, it pointed out that these strains are bile-resistant during this 18 h-period. Growth curves were established in presence of bile salts to determine if the lag phase and the growth rate were affected or not. Assays were undertaken with lactobacilli grown in MRS broth supplemented with 1% reconstituted pet bile, according to the protocol described for earlier growth measurement.

The bifidobacteria were subcultured and grown 32 hours/37° C./anaerobically, using MRS-C broth with 0, 1, 2, 3 and 4% reconstituted pet bile. The same enumeration method at dilutions 1.0E-03, 1.0E-04 and 1.0E-05 was applied as for lactobacilli.

TABLE 4

| | Reconstituted pet bile | | |
|---|---|---|---|
| Compounds | □mol/ml | mg/ml | % total |
| Taurodeoxycholate (Sigma) | 14.00 | 7.00 | 18.0 |
| Taurocholate (Sigma) | 59.00 | 30.40 | 74.0 |
| Cholate (Fluka) | 0.14 | 0.06 | 0.2 |
| Taurachenodeoxycholate (Sigma) | 6.90 | 3.45 | 8.0 |

Survival to Freeze-Drying and Subsequent Storage of the *Lactobacillus* Strains

The evolution of survival was evaluated. Viable counts inferior to 10E+05 CFU/ml were considered as being too low.

For each strain, 200 ml MRS broth was inoculated at 3% with a fresh subculture. The cultures were grown for 16 hours at 37° C. Unaerated conditions (closed containers) were assumed to be essentially anaerobic. Viable cells were enumerated, using the pour-plating method described earlier.

The cultures were harvested by centrifugation at 3,500× g/+7° C./20 minutes (RC3C Sorvall Instrument centrifuge) and resuspended in 10 ml of two different cryoprotective media. Each strain was resuspended in two different cryoprotectants. Concentrated bacterial suspensions were enumerated (pour plating method) and dispensed into vials (0.5 ml per ampoule). The samples were frozen at −196° C. in liquid nitrogen and vacuum dried for 18 hours. After freeze-drying, nitrogen was introduced through the freeze-drier air-admittance valve and all ampoules were sealed. All vials were stored at +4° C. and +20° C. for six months. The number of viable cells per ampoule (for each bacteria and suspension media) was determined monthly.

Results

In the frame of the selection of potential probiotics for cats and dogs, the results of this in-vitro screening of 20 lactobacilli and 18 bifidobacteria, based on their growth potentials, resistance to freeze-drying with subsequent storage, resistance to gastric pH and bile concentrations found in the gastro-intestinal tract of cats and dogs are presented in Table 5.

The 20 lactobacilli were classified with regard to the criteria that they fulfilled in the current study. Four strains showed had good results concerning their growth characteristics, resistance to gastric pH, bile resistance and their survival during storage after to freeze-drying: *L. reuteri* NCC2581 (CNCM I-2448), *L. reuteri* NCC2592 (CNCM I-2450), *L. reuteri* NCC2603 (CNCM I-2451) and *L. reuteri* NCC2613 (CNCM I-2452). The following features were complied:

the generation time was less than one hour when grown in MRS the lag phase was short (less than two hours)

the bacterial counts were high (more than 1.0E+08 CFU/ml) during the stationary phase of the growth cycle and stable at 8 and 24 h post-inoculation the strains were stable through freeze-drying and subsequent six-month storage at 4° C. and 20° C.

the strains were resistant to extreme bile concentration likely to be found in the gastrointestinal tract of cats and dogs (2%)

no significant inhibition in the presence of up to 4% bile in the medium the strains were shown to tolerate pH 2.6 for at least 10 min and could remain at levels higher than 1.0E+08 CFU/ml the strains were resistant to an average gastric pH for at least two hours Therefore, two lactobacilli isolated from cats (*L. reuteri* NCC2581 and *L. reuteri* NCC2592) and two isolated from dogs (*L. reuteri* NCC2603 and *L. reuteri* NCC2613) were selected to be studied for potential probiotic activity.

Strains NCC2581, NCC2592, NCC2603 and NCC2613 were identified as *L. reuteri* by API 50CH identification. However, ribotyping revealed that NCC2581 and NCC2592 had very close patterns, as well as NCC2603 and NCC2613, thus indicating a probable close relationship. Strain NCC2581 had very good growth characteristics and NCC2603 had a better resistance to bile than NCC2613.

Results concerning the eight bifidobacteria isolated from cats feces allowed a selection in function of their growth characteristics, their resistance to gastric pH and their bile sensitivity. Strain NCC2623 had none of the desired characteristics, and would therefore not be recommended for further studies. On the other hand, strain NCC2627 fulfilled all the criteria:

its generation time was less than one hour when grown in MRS-C the lag phase was as short as for lactobacilli counts were high and stable during the stationary phase of the growth cycle the strain was resistant to extreme bile concentration likely to be found in the gastro-intestinal tract of cats and dogs (2%)

no significant inhibition in the presence of up to 4% bile in the medium the strain was shown to tolerate pH 2.6 for at least 10 min and could remain at levels higher than 1.0E+06 CFU/ml the strains were resistant to an average gastric pH for at least two hours The strain NCC2627 was much more resistant than NCC2623 and NCC2635, whereas these three strains had close pattern by ribotyping, therefore indicating a probable close relationship (digestion with two restriction enzymes: EcoRI and EcoRV).

The ten bifidobacteria isolated from dogs showed only two different patterns when characterized by ribotyping. Therefore, bile resistance assays were conducted only with four strains (two from each group): NCC2657, NCC2660, NCC2671 and NCC2677. These four strains were all resistant to maximal concentration of bile that could be found in-vivo (2% bile) and strains NCC2660 and NCC2657 had no decrease in viable counts when subjected to a maximal value of 4% bile. As a consequence, all the bifidobacteria isolated from dogs feces are rather resistant to high concentrations of bile.

Regarding the growth characteristics, these ten bacteria could thereby be divided into two groups:

strains resistant to bile and with good growth characteristics: NCC2657, NCC2651, NCC2663 and NCC2667 strains resistant to bile but with growth characteristics which need to be optimized for industrial production: NCC2660, NCC2671, NCC2677, NCC2647, NCC2654 and NCC2674.

The complete results on resistance to extreme gastric pH found during the digestion of cats and dogs should allow a better determination of the strains to be selected for further studies. Only strain NCC2651 did not fulfill the selection criteria for pH resistance.

TABLE 5

| NCC Code | Code | Growth criteria | Resistance to gastric juice | Resistance to bile | Stability after freeze-drying |
|---|---|---|---|---|---|
| 2578 | LB1-1 | + | + | − | − |
| 2581 | LB1-2 | + | + | + | + |
| 2583 | LK1-1 | + | + | + | − |
| 2586 | LK1-2 | − | + | − | − |
| 2590 | LH2-1 | + | + | + | − |
| 2592 | LR1-1 | + | + | + | + |
| 2594 | LS1-1 | − | + | − | − |
| 2597 | LA2-5 | − | + | + | + |
| 2600 | LC2-5 | − | − | + | − |
| 2603 | LE2-5 | + | + | + | + |
| 2606 | LF2-6 | − | + | + | − |
| 2609 | LH2-6 | + | + | + | − |
| 2613 | LH2-7 | + | + | + | + |
| 2616 | L1-1-1 | − | + | + | − |
| 2619 | L1-1-2 | − | + | + | − |
| 2621 | L3-1-2 | + | + | − | + |
| 2625 | L7-1-3 | + | + | − | + |
| 2628 | LA1-5 | + | + | + | − |
| 2632 | LA1-6 | − | + | + | − |
| 2636 | LB1-5 | − | + | + | + |

With regard to current results, one bifidobacterial strain isolated from cats and three bifidobacteria isolated from dogs (respectively NCC2627, NCC2657, NCC2663 and NCC2667) could be selected.

TABLE 6

| Substrate | Dilution media Composition | | pH |
|---|---|---|---|
| Phosphate buffer | K2PO4 | 72 g·l$^{-1}$ | 7.0 |
| | KH2PO4 | 48 g·l$^{-1}$ | |
| | Distilled water | 1,000 ml | |
| Ringer solution | NaCl | 9 g·l$^{-1}$ | 7.0 |
| | Distilled water | 1,000 ml | |
| TS (Tryptone Saline) | NaCl | 8.5 g·l$^{-1}$ | 7.0 |
| | Tryptone | 1 g·l$^{-1}$ | |
| | Distilled water | 1,000 ml | |

9 ml-portions were dispensed in tubes and autoclaved at 121° C. for 15 min.

Finally, 8 of the 38 strains were selected for further studies (see Example 3): three lactobacilli isolated from cats (NCC2581, NCC2592, NCC2583), three lactobacilli from dogs (NCC2603, NCC2613, NCC2628), one bifidobacteria from cats (NCC2627) and one bifidobacteria from dogs (NCC2657).

These strains are characterized by short generation times, high counts (more than 1.0E+08 cfu/ml) during their stationary phase and stability in high numbers at 8 and 24 h post-inoculation, stability to freeze-drying followed by either storage-conditions, resistance to extreme bile-concentrations found in the duodenum (2% bile) and their low inhibition when grown in presence of up to 4% bile. Furthermore, results from DNA analyses were taken into account to select bacteria representative of the investigated diversity.

Example 3

Efficacy of Colonization in Cats

*L. reuteri* NCC2581, *L. reuteri* NCC2592, *L. rhamnosus* NCC2583 and *Bifidobacterium* sp. NCC2627 were tested in feeding trials so as to evaluate their capacity to survive the passage of the cat gastrointestinal tract.

16 cats male and female as equal as possible were subjected to 3 days of adaptation with Friskies Grand menu boeuf. The feeding protocol consisted in 7 days with "Friskies Grand Menu" and 7 days of test with "Friskies Grand Menu" containing one of the above mentioned strains: *L. reuteri* NCC2581 (diet A), *L. reuteri* NCC2592 (diet B), *L. rhamnosus* NCC2583 (diet C) and *Bifidobacterium* sp. NCC2627 (diet D). The diet assignment was the following:

| Cats n° | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Period 1 | A | D | C | B | D | A | A | C | B | A | B | C | B | D | C | D |
| Period 2 | B | A | D | A | C | C | D | A | C | B | C | D | D | A | B | B |

The said strains were prepared in a sufficient amount and in a stable lyophilized form to apply these eight different bacteria with regard to strain-survival in the gastrointestinal tract of the tested animals. All strains were mixed with 4 g of trehalose in order to add a sufficient volume of carrier for mixing the prepared strains with the food-matrix for the animals. Bacteria strains are prepared in individual plastic tubes (1.0E+09 cfu/day) and daily added in a part of the food to be sure that total bacteria will be eaten.

Fresh fecal samples are obtained to analyze bacterial population numbers and compared with base line (without bacteria added).

Feces are collected on day 7 and 8 (base line),
14 and 15
21 and 22 (base line)
28 and 29.

A sterile rectal probe is used to obtain a fecal sample of at least 0.1 g. This sample is accurately weighted and 0.1 g is mixed with 10 ml of physiological solution (Ringer) containing 10% glycerol. This solution is then transferred into 1 ml cryotubes and frozen in liquid nitrogen. All samples are then stored at
−80° C. until analysis.

The endogenous populations of *Lactobacilli*, Bacteroides, Enterobacteriaceae, Enterococci, Bifidobacteria and *Clostridium perfringens* were counted. Bacteria were detected on selective or semi-selective media. Hundredfold serial dilutions were performed in Ringer solution containing 0.5% of cystein, from the dilutions in the range −2 to −8. Petri dishes of various selective media were inoculated and incubated (see Table below).

| Bacteria | Media | T (° C.) | Time (h) | Atmosphere |
|---|---|---|---|---|
| Enterobacteriaceae | Drigalski (Sanofi Diagnostics Pasteur, France) | 37 | 24 | Aerobic |
| Bifidobacteria | Eugon Tomato* | 37 | 48 | Anaerobic |
| Lactobacilli | MRS (Difco, MI. USA) + antibiotics** | 37 | 48 | Anaerobic |
| Cl. perfringens | NN Agar*** | 37 | 48 | Anaerobic |
| Bacteroïdes | Schaedler Neo-Vanco (BioMérieux, Marcy-l'Etoile, France) | 37 | 48 | Anaerobic |

*Wadsworth Anaerobic Bacteriology Manual, V. Suter, D. Citron and S. Finegold Third ed.
**Phosphomycine (79.5 mg/l) + Sulfamethoxazole (0.93 mg/l) + Trimethoprime (5 mg/l)
***NN agar from Lowbury and Lilly, 1995

Results: The bacterial counts are expressed as log base 10 and presented in Table 7.

During treatment we observe an increase of the fecal counts of lactobacilli, due to the ingestions of the cited probiotic bacteria. We observe no drastic increase in count of Enterobacteriaceae reflecting that there is no damage in the intestinal ecosystem related to the use of the selected probiotics.

Example 4

Efficacy of Colonization in Dogs

*L. reuteri* NCC2603, *L. reuteri* NCC2613, *L. acidophilus* NCC2628 and *Bifidobacterium* sp. NCC2657 were tested in feeding trials so as to evaluate their capacity to survive the passage of the dog gastrointestinal tract.

10 dogs, 5 males and 5 females 4 to 7 years old, were subjected to this specific trial. The feeding protocol consisted in 5 days of adaptation with "Friskies Vitality" w/o chicory and 5 days of test with "Friskies Vitality" w/o chicory and 3 days of adaptation, 5 days of test with "Friskies Vitality" w/o chicory+bacteria: *L. reuteri* NCC2603 (diet E), *L. reuteri* NCC2613 (diet F), *L. acidophilus* NCC2628 (diet G) and *Bifidobacterium* sp. NCC2657 (diet H). The diet assignment was the following:

| dog n° | 1 | 2 | 3 | 4 | 5 | 6 | 7 | 8 | 9 | 10 |
|---|---|---|---|---|---|---|---|---|---|---|
| period 1 | E | E | E | E | E | F | F | F | F | F |
| period 2 | G | G | G | G | G | H | H | H | H | H |

The said strains were prepared in a sufficient amount and in a stable lyophilized form to apply these eight different bacteria with regard to strain-survival in the gastro-intestinal tract of the tested animals. All strains were mixed with 4 g of trehalose in order to add a sufficient volume of carrier for mixing the prepared strains with the food-matrix for the animals. Bacteria strains are prepared in individual plastic tubes (5.0E+09 cfu/day) and daily added in a part of the food to be sure that total bacteria will be eaten.

Fresh fecal samples are obtained to analyze bacterial population numbers and compared with base line (without bacteria added).

Feces are collected on day 7 and 8 (base line),
14 and 15.
21 and 22 (base line)
28 and 29.

A sterile rectal probe is used to obtain a fecal sample of at least 0.1 g. This sample is accurately weighted and 0.1 g is

TABLE 7

| | Fecal bacterial counts in cats (mean ± Stdev, n = 8) | | | | | | | |
|---|---|---|---|---|---|---|---|---|
| | NCC 2581 | | NCC 2592 | | NCC 2583 | | NCC 2627 | |
| | Before | During | Before | During | Before | During | Before | During |
| Lactobacilli | 6.38 ± 2.25 | 7.63 ± 1.23 | 6.12 ± 2.45 | 7.62 ± 1.58 | 5.31 ± 2.04 | 7.47 ± 1.23 | 6.69 ± 1.44 | 7.65 ± 1.45 |
| Bifidobacteria | 7.17 ± 1.82 | 7.64 ± 0.42 | 7.57 ± 1.68 | 6.31 ± 2.26 | 6.43 ± 2.25 | 6.80 ± 2.19 | 8.04 ± 1.03 | 6.07 ± 2.32 |
| Enterobacteriaceae. | 4.25 ± 1.71 | 4.27 ± 1.20 | 4.37 ± 1.35 | 4.58 ± 1.45 | 5.09 ± 1.50 | 4.40 ± 0.63 | 4.59 ± 1.42 | 3.64 ± 0.64 |
| Bacteroides | 6.05 ± 1.38 | 5.54 ± 0.49 | 5.94 ± 0.99 | 6.15 ± 1.43 | 6.19 ± 0.97 | 5.52 ± 0.46 | 6.00 ± 1.11 | 5.48 ± 0.50 |
| C. perfr. | 4.09 ± 1.22 | 3.84 ± 1.00 | 3.61 ± 0.57 | 3.30 ± 0.00 | 4.16 ± 1.64 | 3.34 ± 0.11 | 3.84 ± 0.89 | 3.57 ± 0.56 | mixed with 10 ml of physiological solution (ringer) containing 10% glycerol. This solution is then transferred into 1 ml cryotubes and frozen in liquid nitrogen. All samples are then stored at −80° C. until analysis. The bacteria were counted on the same media that describe in example 3.

Results: The bacterial counts, expressed as log base 10, are presented in Table 8.

TABLE 8

Fecal bacterial counts in dogs (mean ± Stdev, n = 5)

| | NCC 2603 | | NCC 2613 | | NCC 2628 | | NCC 2657 | |
|---|---|---|---|---|---|---|---|---|
| | Before | During | Before | During | Before | During | Before | During |
| *Lactobacilli* | 5.25 ± 1.34 | 3.92 ± 1.05 | 4.00 ± 1.56 | 3.40 ± 0.21 | 7.93 ± 1.75 | 8.30 ± 0.99 | 6.47 ± 1.27 | 7.00 ± 1.35 |
| Bifidobac. | 7.32 ± 2.06 | 4.48 ± 2.64 | 6.09 ± 2.10 | 4.55 ± 2.79 | 7.70 ± 2.57 | 7.20 ± 1.88 | 5.72 ± 2.51 | 6.78 ± 2.39 |
| Enterobact. | 4.10 ± 0.89 | 4.62 ± 0.61 | 3.62 ± 0.72 | 4.39 ± 0.94 | 4.58 ± 1.54 | 4.04 ± 0.76 | 4.51 ± 1.51 | 4.85 ± 1.45 |
| Bacteroides | 7.82 ± 0.53 | 6.70 ± 1.25 | 6.92 ± 1.37 | 6.69 ± 1.19 | 7.88 ± 1.13 | 7.53 ± 0.61 | 7.92 ± 0.63 | 7.66 ± 0.86 |
| *C. perfr.* | 3.70 ± 0.89 | 3.84 ± 0.87 | 3.50 ± 0.45 | 3.30 ± 0 | 3.70 ± 0.62 | 3.30 ± 0 | 3.93 ± 1.25 | 3.70 ± 0.89 |

During treatment we observe no major change in the fecal counts of lactobacilli, due to the ingestions of the selected probiotic bacteria except in the case of the strain *L. acidophilus* NCC2628. Under the tested conditions the inhibitory effect on *C. perfringens* was not significant as the basal level of *C. perfringens* were very low. We observe no drastic increase in count of Enterobacteriaceae reflecting that there is no disturbance of the intestinal ecosystem related to the use of the selected probiotics.

Example 5

Effect of *Lactobacilli* and their Metabolites on the Viability of *Giardia intestinalis*

We studied the effect of culture filtrate supernatants of *Lactobacilli* strains isolated from cats and dogs.

Material and Methods

Bacterial strains and cultures: Micro-organisms belonging to the genus *Lactobacillus* were from the Nestlé Culture Collection. Bacteria were grown in MTYI medium. Supernatants containing metabolites of lactobacilli were neutralized at pH 6 and filter sterilized.

Controls were performed by acidifying MTYI medium with lactic acid to the same pH than the one of the bacterial cultures. Afterwards, pH was adjusted to pH 6 with 0.1 N NaOH. Origin of the strain under study and pH of supernatants and controls are shown in table 9.

TABLE 9

| Strain | Origin | pH supernatant | pH control |
|---|---|---|---|
| *L. reuteri* NCC2581 | Cat | 6.63 | 6.63 |
| *L. rhamnosus* NCC2583 | Cat | 6.50 | 5.97 |
| *L. reuteri* NCC2592 | Cat | 6.04 | 5.98 |
| *L. reuteri* NCC2603 | Dog | 6.04 | 5.99 |
| *L. reuteri* NCC2613 | Dog | 6.07 | 5.95 |
| *L. acidophilus* NCC2628 | Dog | 6.01 | 5.93 |

Parasites: *Giardia intestinalis* strain WB (ATCC 30957) was purchased to American Type Culture Collection (Rockville, USA). Trophozoites were grown in Keister's modified TYI-S-33 medium containing per liter: casein digest (Difco), 20 g; yeast extract (BBL), 10 g; dextrose (Merck), 10 g; bovine bile (Difco), 0.75 g; NaCl (Merck), 2 g; L-cystein. HCl (Sigma), 2 g; ascorbic acid sodium salt (Fluka), 0.2 g; $K_2HPO_4$ (Merck), 0.6 g; ferric ammonium citrate (Sigma), 22.8 mg; adult bovine serum (Sigma), 100 ml; penicillin/streptomycine (Gibco, 1000 IU/ml, 1000 µg/ml), 15 ml. pH was adjusted to 6.9 with NaOH 5N prior to filter sterilization (0.22 µm pore size).

Parasites were cultured in polystyrene tissue culture flasks (LUX, Miles Laboratories, Inc. Naperville Ill. 60540) filled with 40 ml of culture medium. Subcultures were performed by discarding supernatant with non attached parasites, adding 5 ml of ice-cold culture medium, incubating in an ice bath for 10 min to detach adherent trophozoites and inoculating 0.2 ml of the resulting suspension into fresh medium. Incubations were performed at 37° C. in the dark.

Proliferation assays: Two hundred microliters of trophozoite suspensions ($1.4 \times 10^5$ parasites/ml) were mixed with 100 µl of supernatants or controls and 1 µCi of $^3H$ thymidine was added. Samples were incubated at 37° C. for 24 hours in 96-well tissue culture plates (Nunc Brand Products). Then, parasites were harvested and thymidine incorporation was evaluated.

Results

Thymidine incorporation is shown in Table 10. The strain NCC 2628 isolated from a dog produced a strong inhibition of the proliferation of WB strain (91%). Other strains studied did not inhibit trophozoite growth.

TABLE 10

Effect of culture filtrate supernatants on proliferation of *Giardia intestinalis* strain

| Strain | Proliferation *Giardia intestinalis* In CPM |
|---|---|
| *L. reuteri* NCC 2581 | 1720 |
| Control | 2000 |
| *L. rhamnosus* NCC 2583 | 2500 |
| Control | 1720 |
| *L. reuteri* NCC 2592 | 1800 |
| Control | 1970 |
| *L. reuteri* NCC 2603 | 2100 |
| Control | 1900 |
| *L. reuteri* NCC 2613 | 2510 |
| Control | 1950 |
| *L. acidophilus* NCC 2628 | 150 |
| Control | 1610 |
| MTYI | 1870 |

In this experiment it could be demonstrated that functional metabolites produced during growth of *L. acidophilus* NCC 2628 have a very strong inhibitory effect on the growth of *Giardia intestinalis*.

Examples 6 to 8

Inhibitory Effects of *Lactobacillus* Strains According to the Invention on Intestinal Pathogenic Bacteria To identify strains with strong antagonistic properties against small intestinal pathogens, co-cultivation experiments were performed in a model system simulating canine small intestinal conditions (pH, bile composition and concentration, mucin, pancreatin). Simulated canine small intestinal juice contained reconstituted canine bile (0.345 g/l taurochenodeoxycholate, Sigma, Germany; 0.7 g/l taurodeoxycholate, Sigma, Germany; 3.04 g/l taurocholate, Sigma, Germany; 0.006 g/l cholate Fluka, Switzerland), porcine mucine (1.9 g/l Sigma, Germany), porcine pancreatin (2.42 g/l, Sigma, Germany) and electrolyte solution (5 g/l NaCl, 0.6 g/l KCl, 0.25 g/l CaCl$_2$, all Merck, Germany). The pH of the juice was adjusted to pH 6.5±0.5 with 0.1 N NaOH.

Strains and Cultivation Conditions

Small Intestinal Pathogens

Four potentially pathogenic strains were selected: *S. typhimurium* SL1344, *E. coli* ETEC O8:H9 and *E. coli* O149:K88 (pathogenic canine isolate) and a clinical isolate of *Sh. dysenteriae* (human origin, kindly provided by Centre Hospitalier Universitaire Vaudoise—CHUV Lausanne, Switzerland). With the exception of *S. typhimurium* SL1344 propagated in Luria Bertani broth (Difco, USA), all enterobacteriaceae were grown in Brain Heart Infusion broth (Difco, USA) at 37° C. under shaking (240 rpm).

Lactic Acid Bacteria

A wide range of lactobacilli of canine and feline origin including *L. acidophilus* NCC2628 (CNCM I-2453), *L. rhamnosus* NCC2583 (CNCM I-2449), *L. reuteri* NCC2581 (CNCM I-2448), *L. reuteri* NCC2592 (CNCM I-2450) were selected from the Nestlé Culture Collection (NCC, Nestec, Switzerland) and screened in the canine small intestinal model for survival, physiological activity and inhibitory effects on above mentioned small intestinal pathogens. *Lactobacilli* were cultured anaerobically (anaerocult, Oxoid, England) in Man Rogosa Sharp broth (Difco, USA) at 37° C.

Determination of Viable Cell Counts

Samples were diluted in sterile phosphate buffer (NaH$_2$PO$_4$, pH 7, 0.2 M) and surface plated of 10-fold dilutions on agar plates: MRS agar (Difco, USA) for lactobacilli, *Salmonella-Shigella* agar (Oxoid, England) for *S. typhimurium* and *Sh. dysenteriae*, and Sorbitol Mac Conkey agar (Oxoid, England) for *E. coli*. Agar plates were incubated 48 hours at 37° C. anaerobically for lactobacilli, and 24 hours at 37° C. for enterobacteriaceae. For co-cultivation trials, the growth of enterobacteriacea on MRS agar was inhibited by addition of polymixin (Oxoid, England).

Co-Cultivation Experiments Between Lactic Acid Bacteria (LAB) and Pathogens

Co-cultivation experiments with potential probiotic LAB and pathogenic strains were performed at 37° C. in 20 ml (Falcon tubes) simulated canine small intestinal juice enriched with different carbon sources (sugar, pet food) to favor metabolic activity of the cultures. LAB were inoculated at 10E+08 cfu/ml, pathogens at 10E+02 cfu/ml, 10E+04 cfu/ml and 10E+06 cfu/ml. Samples were taken at different time points up to 8 hours and viable cell counts were determined by surface plating of 10-fold dilutions on respective media.

Co-cultivation trials were performed under different conditions including enrichment of simulated canine small intestinal juice with dextrose (5 g/l) and different concentrations of commercially available extruded dry pet food (5, 25 or 100 g/l; Friskies ALPO Complete, USA). The latter was homogenized (Stomacher Lab Blender) and suspended in electrolyte solution. All experiments were performed in duplicate.

Example 6

Co-cultivation experiments between four lactobacilli and the four potentially pathogenic strains *E. coli* ETEC O8:H9, *E. coli* O149:K88, *S. typhimurium* SL1344 and *Sh. dysenteriae* were performed in simulated canine duodenal juice enriched with 5 g/l dextrose (Difco). *Lactobacilli* were inoculated at 10E+08 cfu/ml and the Gram negative indicator strains at 10E+02 cfu/ml. Results are compiled in Table 11.

TABLE 11

Co-cultivation between LAB and potentially pathogenic bacteria in simulated canine small intestinal juice enriched with dextrose

| PROBIOTIC | Pathogen | | | |
|---|---|---|---|---|
| | *E. coli* ETEC O8:H9 | *E. coli* O149:K88 | *S. typhimurium* SL1344 | *Sh. dysenteriae* |
| *L. acidophilus* NCC2628 (CNCM I-2453) | +++ | +++ | +++ | +++ |
| *L. rhamnosus* NCC2583 (CNCM I-2449) | +++ | +++ | +++ | +++ |
| *L. reuteri* NCC2581 (CNCM I-2448) | No inhibition | ++ | No inhibition | +++ |
| *L. reuteri* NCC2592 (I-2450) | No inhibition | ++ | No inhibition | + |

\+ Inhibition of growth
++ Inhibition of growth and partial inactivation
+++ Inhibition of growth and complete inactivation All four investigated lactobacilli demonstrated antimicrobial activity but only *L. acidophilus* NCC2628 (CNCM I-2453) and *L. rhamnosus* NCC2583 (CNCM I-2449) demonstrated high activity against all tested pathogens. Both strains were not only able to inhibit the growth, but were also able to completely inactivate the pathogens contained in the test system (no remaining viable cells).

Example 7

Co-cultivation experiments were performed between *lactobacilli* [(*L. acidophilus* NCC2628 (CNCM I-2453), *L. rhamnosus* NCC2583 (CNCM I-2449) and *S. typhimurium* SL1344 in simulated canine duodenal juice enriched with commercially available extruded dry pet food (5, 25 or 100 g/l; Friskies ALPO Complete, USA). *Lactobacilli* were inoculated at 10E+08 cfu/ml and the Gram negative indicator strains at 10E+02 cfu/ml. Results are compiled in Table 12.

TABLE 12

Co-cultivation between LAB and potentially pathogenic bacteria in simulated canine small intestinal juice enriched with dry pet food

| PROBIOTIC | Enrichment with pet food | Pathogen S. typhimurium SL1344 |
|---|---|---|
| L. acidophilus NCC2628 | 5 g/l | +++ |
| (CNCM I-2453) | 25 g/l | +++ |
|  | 100 g/l | +++ |
| L. rhamnosus NCC2583 | 5 g/l | No inhibition |
| (CNCM I-2449) | 25 g/l | + |
|  | 100 g/l | ++ |

+ Inhibition of growth
++ Inhibition of growth and partial inactivation
+++ Inhibition of growth and complete inactivation Results demonstrate the high potential of especially *L. acidophilus* NCC2628 (CNCM I-2453) to inhibit the growth and even to inactivate completely small intestinal pathogens under very practical conditions such as in a mix of simulated small intestinal juice and pet food. The antimicrobial activity of *L. acidophilus* NCC2628 was very high even at low levels of enrichment with commercial pet food serving as a source of fermentable sugars for the organism. In contrast this observation made for *L. acidophilus* NCC2628 the effectiveness of *L. rhamnosus* NCC2583 (CNCM I-2449) was depending on the level of enrichment with pet food in that way that an increasing antimicrobial activity was observed with increasing amounts of pet food added to the test system.

Example 8

Co-cultivation experiments with *L. acidophilus* NCC2628 (CNCM I-2453) and different inoculation levels of *S. typhimurium* SL1344 were performed in simulated canine duodenal juice enriched with dextrose (5 g/l, Difco). *L. acidophilus* NCC2628 (CNCM I-2453) was inoculated at 10E+08 cfu/ml, *S. typhimurium* SL1344 was inoculated at 10E+02 cfu/ml, 10E+04 cfu/ml and 10E+06 cfu/ml. Results are compiled in Table 13.

TABLE 13

Co-cultivation of L. acidophilus NCC2628 (CNCM I-2453) and different inoculation levels of S. typhimurium SL1344

| PROBIOTIC | Inoculation level of the pathogen | Pathogen S. typhimurium SL1344 |
|---|---|---|
| L. acidophilus | 10E+02 cfu/ml | +++ |
| NCC2628 | 10E+04 cfu/ml | +++ |
| (CNCM I-2453) | 10E+06 cfu/ml | +++ |

+ Inhibition of growth
++ Inhibition of growth and partial inactivation
+++ Inhibition of growth and complete inactivation The antimicrobial activity of *L. acidophilus* NCC2628 (CNCM I-2453) was sufficiently high to completely inactivate even high initial concentration of *S. typhimurium* SL1344.

Example 9

In-Vivo Immune Stimulation in Dogs

The immune stimulating potential for pet-isolated strains of probiotics was tested in a clinical trial using the *L. acidophilus* NCC 2628 strain.

Methods:

Canine Peripheral Blood Mononuclear Cells (PBMC) Proliferation Upon Stimulation with Different Mitogens:

20 dogs 4 to 7 years old were subjected to this trial. The feeding protocol consisted in one week of adaptation with "Friskies Vitality" w/o chicory and 4 weeks of test with "Friskies Vitality" w/o chicory+*L. acidophilus* NCC2628 bacteria.

*L. acidophilus* NCC2628 was prepared in a sufficient amount and in a stable lyophilized form with regard to strain-survival in the gastro-intestinal tract of the tested animals. Bacteria were mixed with 4 g of trehalose in order to add a sufficient volume of carrier for mixing the prepared bacteria with the food-matrix for the animals. Bacteria were prepared in individual plastic tubes (5.0E+09 cfu/day) and daily added in a part of the food to be sure that total bacteria will be eaten.

Blood was collected from the dogs after the four weeks of probiotic administration. The blood was fractionated through a Vaccutainer™ column (Becton Dickinson, Mountain View, Calif.). PBMC were recovered according to the manufacturer's recommendations.

Cells were stimulated with different mitogens or phorbol esters that induce a strong proliferation of T cells (concanavalin A (conA), Phytohemaglutinin (PHA)), of B cells (Pokeweed mitogen (PWM)), and of all cells (Phorbol-Myristate-Acetate/Ionomycine (PMA/Iono)). $10^5$ cells per well were incubated with mitogens or the phorbol esters (the respective doses are indicated in the FIG. 1) in a final volume of 200 □l of RPMI-1640 culture medium supplemented with 10% fetal calf serum and antibiotics in 96-well flat-bottom culture plates (Nunc).

Cells were maintained in humidified 5% $CO_2$ atmosphere at 37° C. for 48 h. The cells were pulse-labelled with 1 □Ci of [$^3$H]thymidine (Amersham Pharmacia Biotech, Switzerland) for a further 18 h. The cells were then harvested on nitrocellulose filters (Packard) and bound [$^3$H]thymidine was measured by scintillation counting (TopCount; Packard, Switzerland). Cell proliferation was calculated as the mean (counts per minute (c.p.m) (±SD) from triplicates.

Figure 1:
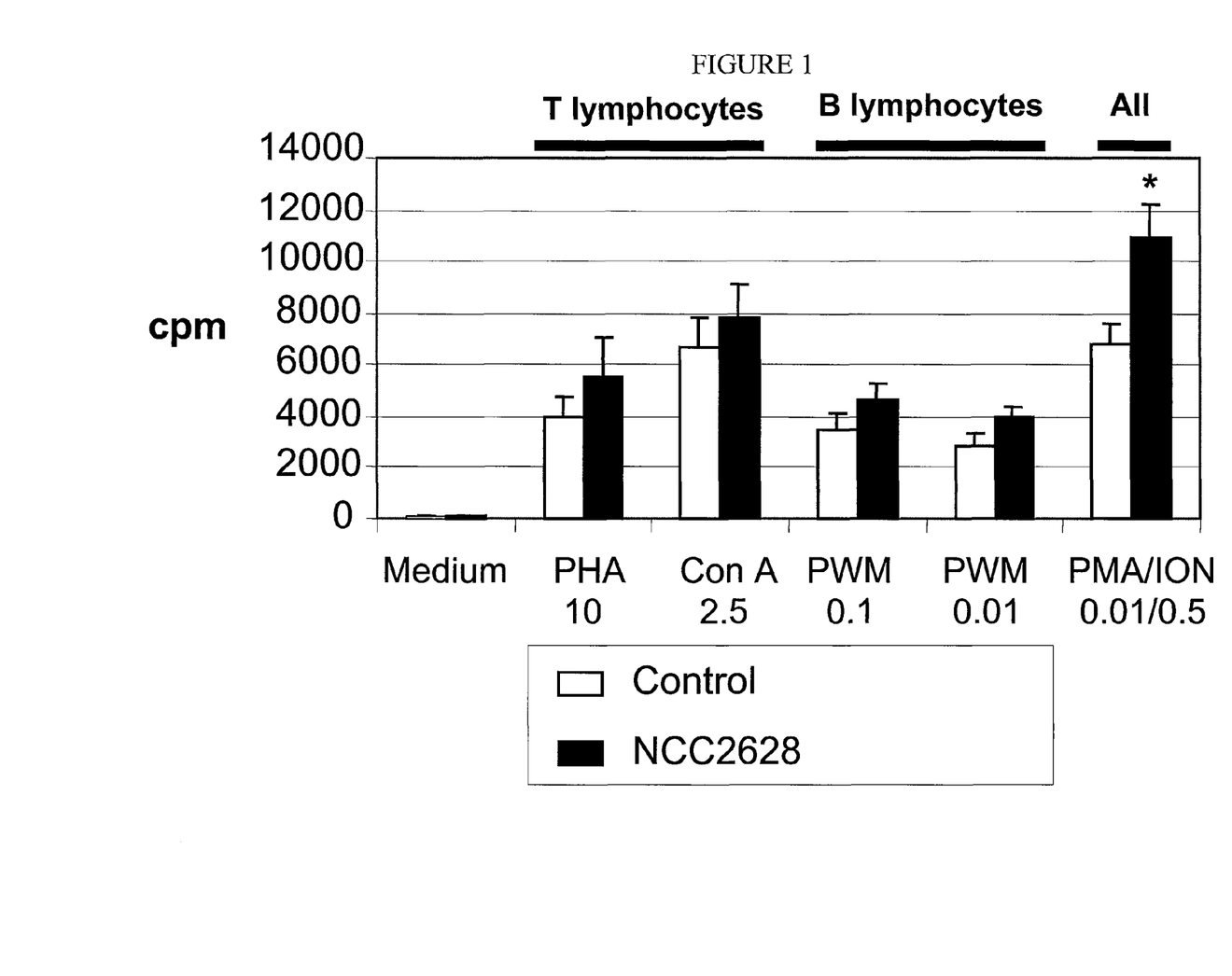
FIG. 1: Lymphocyte proliferation of canine peripheral blood mononuclear cells (PMBC) upon stimulation with mitogens or phorbol esters. PMBC from adult dogs fed during 4 weeks with (Black bars) or without (White bars) *L. acidophilus* NCC2628 were stimulated with different mitogens at doses (μg/ml) indicated in the graphic. Mitogens are PHA (Phytohemaglutin), ConA (Concanavalin A), PWM (Pokeweed mitogen) and phorbol ester are PMA/iono (Phorbol myristate acetate and ionomycin). *=P<0.05, Student's t test.

Results:

FIG. 1: There was a clear increase in cell proliferation in response to all mitogens in the group of dog fed with. *L. acidophilus* NCC2628 compared with the control group. This increase was significant in cultures stimulated with the phorbol esters PMA+ionomycin. This data shows that lymphoid cells from probiotic-fed dogs were more reactive upon activation in vitro and suggests that the immune system of probiotic-fed dogs has been stimulated.

Example 10

In Vitro Modulation of Immune Functions by Pet-Isolated *Lactobacillus* Strains

An in-vitro screening of the different pet-isolated *lactobacillus* strains described above was setup to determine their immune modulation potential. To this end, we measured their ability to induce pro-inflammatory cytokines (IL-12, IFN□) and/or anti-inflammatory cytokines (IL-10, TGF-□) (Anand A. C., Adya C. M. 1999, *Trop. Gastroenterol.;* 20(3):97-106; Spellberg B., Edwards J. E. Jr 2001, *Clin. Infect. Dis.;* 32(1): 76-102.). This aimed at selecting potential candidate strains for strong anti-pathogenic or anti-cancer immune functions as well as antagonistic functions against canine intestinal pathologies such as allergy and inflammation (Inflammatory bowel diseases). Additional cultures were set up with medium alone (negative control), with *Enterococcus faecium* strain SF68 (NCIMB 10415, Cerbios-Pharma, Switzerland) and with a human *lactobacillus* isolate ST11 (NCC 2461; CNCM I-2116) (positive control).

Method:

Cytokine Profiles Induced by Different Probiotic Strains in Canine Leukocytes:

Blood from normal adult dogs was treated 5 min at room temperature with ACK lysing buffer (150 mM of $NH_4Cl$, 1 mM of $KHCO_3$, and 0.1 mM of $Na_2EDTA$ in $H_2O$, pH=7.4). The leukocytes were washed twice with RPMI medium (without antibiotics) and seeded at $2.10^6$ cell/ml into 24-well tissue culture plates. 1 ml of a bacterial suspension (described bellow) containing $10^6$ CFU was added to each well.

Figure 2:
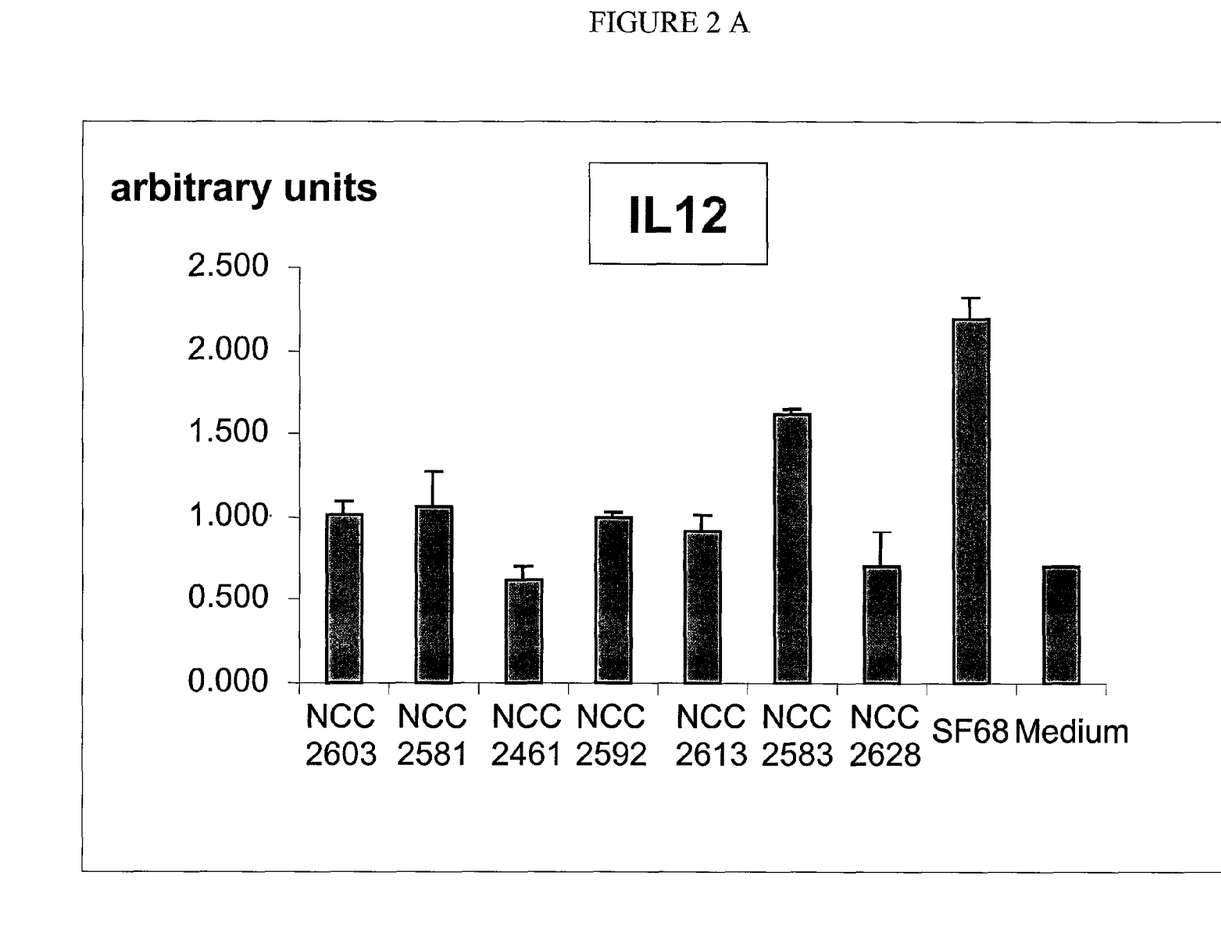
FIG. 2: Cytokines produced by canine leucocytes stimulated with different strains of probiotics. Leucocytes from normal adult dogs were stimulated with different pet-isolated *lactobacillus* strains for 18 h. Control cultures contained medium alone (negative control) or a human *lactobacillus* isolate ST11 (positive control). Identification of cytokines was done by RT-PCR. Their quantification was performed by scanning the ethidium bromide-strained agarosgels and determining the relative pixel of each band using the NIH Image software. The results are expressed as the means of two independent experiments in arbitrary units. (A) IL-12, (B) IL-10, (C) IFNγ, (D) TGFβ.

For control treatment, medium alone was added to the leukocytes. The samples were incubated 18 h at 37° C. and 5% $CO_2$. Subsequently, leukocytes were collected, washed in PBS and centrifuged. The cell pellet was lysed with 500 □l of Trizol reagent (Gibco BRL). RNA was extracted from cellular lysates using the Nucleospin RNA kit (Macherey-Nagel). RT-PCR for canine cytokine amplifications were performed using the AB gene kit (Merck). The primer references (all produced by Microsynth) are indicated bellow. Densitometric analysis of the PCR-bands revealed in the ethidium bromide-stained agarose gels was performed using the NIH Image software. All bands were normalised with the respective □-actin PCR-product band obtained with each sample (internal control), and the results are expressed as arbitrary units reflecting the pixel densities of each cytokine PCR-product band (FIG. 2).

Preparation of the bacteria: the different strains of *lactobacilli* were grown in MRS medium for approximately 8 h until they reached identical density. The bacteria were diluted in RPMI medium without antibiotics to final concentrations of $10^6$ CFU/ml.

Primers used for cytokine—RT-PCRs:

| Cytokines | References |
|---|---|
| IL-12p40 | Büttner M., et al. 1998. Cytokine; 10(4): 241-248. |
| IFN□ | Büttner M., et al. 1998. Cytokine; 10(4): 241-248. |
| TGF□1 | Gröne A., et al. 1998. Vet. Immunol. Immunopathol.; 65: 11-27. |
| IL-10 | Pinelli E., et al., 1999, Vet. Immunol. Immunopathol.; 69: 121-126. |

Results:

FIG. 2: The data show that cytokine profiles induced by *lactobacilli* are strain-dependent. For example, the strain NCC2628 induced high levels of IL-10 and TGF-□, highlighting the potential for this particular strain for the immune modulation of inflammatory disorders such as allergy and inflammatory bowel diseases. In contrast, the strain NCC2583 induced strong levels of IFN□ and IL-12, which makes this strain a good candidate for anti-pathogenic or anti-cancer activity.

Example 11

Three dried pet foods are used in the study. These will be referred to as "A", "B" and "C". Pet food "A" is a nutritionally complete dried pet food, available under the brand name ALPO (ALPO is a registered trade mark of SOCIETE DES PRODUITS NESTLE S.A. of Switzerland).

Pet food B is the same nutritionally complete dried pet food as Pet Food A, but is supplemented with a powdered mixture of selected probiotic micro-organisms fed from a sachet. The mixture comprises substantially equal amounts of *L. acidophilus* NCC2628 and *bifidobacterium* sp. NCC2657. It is sprinkled over the food at each meal serving, the dosage supplied being about 1.0E8 cfu/day.

Pet food C is a nutritionally complete dried pet food which is substantially identical to Pet Food A but which contains 1.2% by weight of a dried supernatant of a culture of *Enterococcus faecium* SF68 (NCIMB 10415).

30 dogs are used in the study. The dogs are pre-fed for 8 weeks using Pet Food A. The dogs are then divided into 3 groups of 10 dogs each, designated groups A, B and C and fed the correspondingly-named diets for 8 weeks:

The dogs have free access to water and are fed once a day. The prevalence of dandruff in the coat is determined by a 30 member evaluation panel at commencement and then at 7 weeks later.

The dogs are groomed prior to evaluation by the panel and the panel members do not compare notes during the evaluation.

In this evaluation the dogs are presented to each of the individual panelists in 20 different pairings. The panelists are asked to indicate on a their scoresheets which dog of the pair presented displays (1) less dandruff (2) higher coat gloss and (3) less coat odour.

The overall coat condition of all dogs is visually and tactilely good as can be expected of normal, healthy dogs. However, the dogs which are fed diet C are found to have noticeably less dandruff than those fed on control diet A. Those fed on diet B have noticeably glossier coat and exhibit less noticeable coat odour than those on A. These characteristics are found not to differ significantly statistically when compared with the dogs in group B.

Example 12

A feed mixture is made up of about 58% by weight of corn, about 6% by weight of corn gluten, about 23% by weight of meat and meal, salts, vitamins and minerals making up the remainder.

The feed mixture is fed into a preconditioner and moistened. To this mixture is added a powder containing a mixture of the following *Lactobacillus* strains: *Lactobacillus rhamnosus* NCC2583 (CNCM I-2449), *Lactobacillus acidophilus* NCC2628 (CNCM I-2453) and *Enterococcus faecium* SF68 (NCIMB 10415). The powder is substantially homogeneously dispersed throughout the mixture. This moistened feed mix is then fed into an extruder-cooker and gelatinised. The gelatinised matrix leaving the extruder is forced through a die and extruded. The extrudate is cut into pieces suitable for feeding to clogs, dried at about 110° C. for about 20 minutes, and cooled to form pellets. The extrudate pieces are checked for bacterial activity of the added strains. None is detected.

Example 13

24 dogs are used in this study. They include younger and older dogs, the latter being from 8 to 12 years in age. The older dogs selected, exhibit external signs of joint inflammation commensurate with their ages and appear to experience some difficulty in moving at times. Certain movements appear to be painful. These symptoms are often observed in older dogs and are believed to relate to arthritic condition.

Three dried pet foods are used in the study, designated A, B and C. Pet food A is a nutritionally complete dried pet food (ALPO Beefy Dinner). This is the control food.

All 24 members of the selected are pre-fed for 8 weeks using Pet Food A. The dogs are then divided into 3 groups, A, B and C each having 8 dogs and the same proportion of younger and older within. Each group is then fed the following respective diets for 8 weeks:

| Group | Pet Food |
|-------|----------|
| A | A |
| B | B |
| C | C |

Pet food B is a nutritionally complete dried pet food which is substantially identical to Pet Food A but which contains has a coating making up 2% of its weight, the coating comprising the micro-organisms of *Enterococcus faecium* SF68 (NCIMB 10415). The quantity of food fed daily to each dog is calculated according to individual body mass, so that the dosage of 1.0E+09 cfu/day.

Diet C comprises the extruded kibbles produced in example 12 above. The quantity of food fed daily to each dog is calculated according to individual body mass, so that the micro-organism dosage is 1.0E+11 cfu/day.

The dogs have free access to water and are fed once a day. An activity meter is attached to the collar of each dog and measurements are taken daily. The dogs are also visually evaluated for activity by kennel staff.

The condition of all dogs is visually and tactilely good as can be expected of normal, healthy dogs. However, the dogs in the groups that receive pet food diets B and C are noticeably more active than their counterparts on diet A. Meter readings support these observations.

Further, the elderly dogs in groups B and C, after being fed diets B and C for the trial period, appear to exhibit fewer external signs of local joint inflammation. Further, the dogs appear to experience lower levels of pain on physical movement and move more freely than before. It can be concluded that diets B and C appear to provide relief with respect to certain signs of ageing and improve the motility of older pets.

Example 14

Dry Cat Food

A feed mixture is made up of about 58% by weight of corn, about 6% by weight of corn gluten, about 23% by weight of chicken meal, salts, vitamins and minerals making up the remainder.

The feed mixture is fed into a preconditioner and moistened. The moistened feed is then fed into an extruder-cooker and gelatinised. The gelatinised matrix leaving the extruder is forced through a die and extruded. The extrudate is cut into pieces suitable for feeding to cats, dried at about 110° C. for about 20 minutes, and cooled to form pellets. At this point, a lyophilized powder of one or more strains of the following *Lactobacillus* species is provided for application to the pellets: *Lactobacillus rhamnosus* NCC2583 (CNCM I-2449), *Lactobacillus acidophilus* NCC2628 (CNCM I-2453) or *Enterococcus faecium* SF68 (NCIMB 10415). Sufficient powder is thus provided so that the corresponding dietary intake amount for the cat is from about 1.0E+07-1.0E+9 cfu/day. Some of the powder is mixed into a first mass of pellets and bagged. A second quantity of the powder is measured out and mixed with a lipid carrier which is then sprayed on to a second mass of pellets. The pellets are bagged after the coating has dried sufficiently at 50-60° C. for some minutes Example 15

Canned Pet Food and Supplement

A mixture is prepared from 73% of poultry carcass, pig lungs and beef liver (ground), 16% of wheat flour, 2% of dyes, vitamins, and inorganic salts. This mixture is emulsified at 12° C. and extruded in the form of a pudding which is then cooked at a temperature of 90° C. It is cooled to 30° C. and cut in chunks. 45% of these chunks are mixed with 55% of a sauce prepared from 98% of water, 1% of dye and 1% of guar gum. Tinplate cans are filled and sterilized at 125° C. for 40 min. As a probiotic supplement to be mixed with the pet-food before serving, additional packaging in sachet form with strains of the following *Lactobacillus* species are provided *Lactobacillus rhamnosus* NCC2583 (CNCM I-2449), *Lactobacillus acidophilus* NCC2628 (CNCM I-2453) or *Enterococcus faecium* SF68 (NCIMB 10415). The corresponding amount for the pet is from about $10^6$-$10^{12}$ cfu/day, depending on whether a cat or a dog and on physical factors such as body mass. This is supplied as a supplement with removably attached to the can, together with feeding directions.

The invention claimed is:

1. A method of maintaining or improving health of a gastrointestinal tract of a pet, the method comprising administering a pet food composition to the pet wherein the pet food composition comprises an isolated strain of lactic acid bacteria having an effective amount of probiotic activity and is capable of colonizing or surviving in the gastrointestinal tract, wherein the isolated strain is selected from the group consisting of *Lactobacillus reuteri* NCC2581 (CNCM I-2448), *Lactobacillus reuteri* NCC2592 (CNCM I-2450), *Lactobacillus rhamnosus* NCC2583 (CNCM I-2449), *Lactobacillus reuteri* NCC2603 (CNCM I-2451), *Lactobacillus reuteri* NCC2613 (CNCM I-2452), *Lactobacillus acidophilus* NCC2628 (CNCM I-2453), *Enterococcus faecium* SF 68 (NCIMB 10415) and combinations thereof.

2. The method according to claim 1, wherein the isolated strain further comprises at least one of a supernatant of a culture thereof and a metabolite thereof.

* * * * *